(12) United States Patent
McCarthy (10) Patent No.: US 8,308,815 B2
(45) Date of Patent: Nov. 13, 2012

(54) VACUUM-ASSISTED LINER SYSTEM

(75) Inventor: Joseph R. McCarthy, Hamshire (GB)

(73) Assignee: Blatchford Products Limited, Hampshire (GB)

( * ) Notice: Subject to any disclaimer, the term of this patent is extended or adjusted under 35 U.S.C. 154(b) by 45 days.

(21) Appl. No.: 12/811,895

(22) PCT Filed: Jan. 21, 2009

(86) PCT No.: PCT/GB2009/000162
§ 371 (c)(1),
(2), (4) Date: Sep. 29, 2010

(87) PCT Pub. No.: WO2009/093020
PCT Pub. Date: Jul. 30, 2009

(65) Prior Publication Data
US 2011/0035027 A1  Feb. 10, 2011

(30) Foreign Application Priority Data
Jan. 21, 2008  (GB) .................................. 0801065.4

(51) Int. Cl.
*A61F 2/80*  (2006.01)
(52) U.S. Cl. ........................................... 623/34; 623/36
(58) Field of Classification Search .................... 623/33, 623/34, 36; 602/62, 63; *A61F 2/78, 2/80*
See application file for complete search history.

(56) References Cited

U.S. PATENT DOCUMENTS
| | | | |
|---|---|---|---|
| 2,634,424 A | 4/1953 | O'Gorman | |
| 3,309,714 A | 3/1967 | Porten | |
| 2001/0016781 A1* | 8/2001 | Caspers | 623/34 |
| 2001/0039159 A1 | 11/2001 | Janusson et al. | |
| 2004/0181290 A1* | 9/2004 | Caspers | 623/34 |

(Continued)

FOREIGN PATENT DOCUMENTS
EP    0 182 412 A1    5/1986
(Continued)

OTHER PUBLICATIONS

International Search Report and Written Opinion for International Appl. No. PCT/GB2009/000162, mailed Aug. 21, 2009.

(Continued)

*Primary Examiner* — Corrine M McDermott
*Assistant Examiner* — Randy Shay
(74) *Attorney, Agent, or Firm* — Alston & Bird LLP (57) ABSTRACT

A vacuum-assisted liner system for the socket of a limb prosthesis secures the prosthesis to a residual body portion. A vacuum is created directly between the residual body portion and the socket (8) to hold them together and minimize relative movement between them. The system includes a flexible liner (4) made of an impermeable material, at least a distal part (4D) of the liner being porous to allow the transport of air and fluid directly away from the residual body portion to the outer surface of the liner. A fabric distribution layer (6) is located over the liner (4) and between the liner and the socket (8) to allow transmission of such extracted air and fluid laterally over the liner to an evacuation port (10) in the socket. Also disclosed is a limb apparatus suspension device incorporating the liner system, and a vacuum suspension device which secures a component such as a stamp socket to a residual body portion by creating an evacuated space sealed by intimate contact directly between the socket (8) and a boundary region of the liner (4).

12 Claims, 6 Drawing Sheets

U.S. PATENT DOCUMENTS

| | | | |
|---|---|---|---|
| 2004/0260403 A1* | 12/2004 | Patterson et al. ............... | 623/34 |
| 2007/0225824 A1 | 9/2007 | Einarsson | |
| 2010/0023134 A1 | 1/2010 | Laghi | |

FOREIGN PATENT DOCUMENTS

| | | |
|---|---|---|
| WO | WO 01/70147 | 9/2001 |
| WO | WO-2007/030609 A2 | 3/2007 |
| WO | WO 2009/017762 A1 | 2/2009 |
| WO | WO 2009/042240 A1 | 4/2009 |
| WO | WO 2009/093020 A1 | 7/2009 |
| WO | WO 2010/141960 A2 | 12/2010 |

OTHER PUBLICATIONS

Masi et al., "Active Ventilation of Above- and Below-Knee Prosthetic Devices," *Proceedings of the 1990 16$^{th}$ Annual Northeast Bioengineering Conference*, Mar. 26-27, 1990, pp. 25-26.

Search Report for British Application No. GB 1021829.5, dated Feb. 25, 2011.

Search Report for British Application No. GB 1122135.5, dated Mar. 23, 2012.

Search Report for British Application No. GB 1122135.5, dated Aug. 6, 2012.

* cited by examiner

VACUUM-ASSISTED LINER SYSTEM

The present invention relates to a vacuum-assisted liner system for use in a suspension device which is to be attached to a human body portion forming part of or associated with a limb, the invention also relates to a vacuum-assisted suspension device for a limb prosthesis, and to such a suspension device for a limb orthosis. The invention is particularly applicable to a vacuum socket assembly for attaching a limb prosthesis to a residual body portion. More particularly, the invention provides a new assembly and system for securing a prosthetic device to a residual body portion for a transtibial amputee.

Maintaining an intimate fit between a residual body portion and the socket of a prosthetic limb is known to cause problems with the comfort and control of the limb prosthesis. It is known that these problems are, in part, due to the occurrence of relative movement between the residual body portion and the socket. Typically, this relative movement causes abrasions on the residual body portion and increased energy consumption during ambulation, as well as a lack of control of the prosthetic device.

It is known to improve the comfort of the amputee by employing a liner made from a visco-elastic material, the liner being positioned between the residual body portion and the socket. Unfortunately, such liners do not "breathe" as they create an airtight seal with the residual body portion. This seal can then be used to suspend a prosthetic device. Various methods have been devised to suspend a prosthetic device from a liner. For example, a pin may be attached directly between the distal surface of the liner and the socket. Alternatively, suspension can be achieved using a flexible non-porous sleeve that is fitted externally so as to overlap the brim of the socket and to engage the wearer's skin above the socket brim thereby to create an air-tight seal.

Although the known methods can reduce relative movement of the residual body portion with respect to the prosthetic device thereby improving comfort for the amputee, they still permit a significant amount of relative movement.

Several innovations over recent years have sought to restrict relative movement between a residual body portion and a prosthesis further by applying an active vacuum via the liner to the residual body portion. An active vacuum is defined as one that is less than atmospheric pressure and is generated by, usually, either a mechanical or electrically powered vacuum pump. It is known to use such a vacuum pump in combination with a non-porous liner that effectively insulates and seals off air flow to the residual body portion. By ensuring an intimate fit of the liner to the residual body portion and evacuating the space between them using the vacuum pump, it is possible to secure the liner to the residual body portion purely by vacuum while minimising relative movement between the residual body portion and the liner. It is then possible to secure the liner to the socket of a prosthetic device. The Otto Bock Harmony® system is an example using this technique.

Another known liner system is the Iceross® Seal-In liner which is configured such that a vacuum is created when the residual body portion, covered by the liner, is pushed into the socket.

One difficulty encountered with all liners made of materials such as silicone is that, in a hot environment or during exertion, sweating results which allows relative movement between the residual body portion and the liner or the prosthetic device. Additionally, sweating creates a moist environment which softens the skin and provides a breeding ground for pathogens. The consequences of this are that the residual body portion is more prone to abrasion, tissue breakdown and infection. Ideally, relative motion between the skin and the socket interface should be eliminated.

It is known from WO 2007/030609 (King) to provide an inner fabric layer to act as a wicking layer between the tissue of the residual body portion and the liner. This fabric layer allows an active vacuum to propagate around the surface of the residual body portion and thereby assists in securing the liner and prosthetic device to the residual body portion. Furthermore, this wicking layer promotes the removal of fluids such as sweat from the surface of the residual body portion. Nevertheless, the potential for harbouring bacteria remains. In addition, the fabric layer can cause abrasion and damage of the tissue of the residual body portion with any relative movement.

U.S. Pat. No. 6,544,292 (Laghi) discloses a soft gel liner with a fabric-covered exterior.

EP0182412A (Jongenengel) discloses a leather artificial limb socket having a thin flexible leather inner layer and a leather outer layer, the leather layers sandwiching therebetween a resilient thermoplastics layer bonded to the inner leather layer and having perforations which aid in the dissipation of heat and moisture from the residual limb enclosed by the socket.

US2001/0016781A (Capsers) discloses an example of a vacuum-assisted suspension socket having a flexible suspension sleeve overlapping the brim of the socket. Inside the socket, a sealed cavity is formed between the socket and a liner which is coextensive with the socket. Inside the liner is an osmotic membrane encasing the residual limb portion and, between the liner and the socket, there is a sheath of knitted nylon to aid fitting of the socket over the liner.

It is an object of this invention to provide an improved vacuum-assisted liner system and suspension device.

According to a first aspect of the invention, a vacuum-assisted liner system for use in a suspension device which is to be attached to a human body portion forming part of or associated with a limb comprises: a flexible liner to be fitted over the body portion and having at least one peripheral edge, the liner being made of a material impermeable to air and having a porous section spaced from the or each peripheral edge to allow transmission of air and moisture between an outer surface and an inner surface of the liner; and a porous distribution layer overlying the outer surface of the liner and adapted to allow transmission of air and moisture transversely over the said outer surface through the layer. Using such a liner system, it is possible, when an outer suspension device wall member, e.g. a socket, is fitted over the liner system, to create a vacuum directly between the residual body portion and the socket thereby to suspend a prosthetic device from the residual body portion whilst minimising the potential for relative movement between them. The vacuum is transmitted to the residual body portion through the porous section of the liner, the majority of the space between the liner and the socket being occupied by the distribution layer so that the vacuum created by evacuating the socket is transmitted over most of the area of the liner causing the liner to adhere to the inside of the socket over a wide area. The distribution layer allows air and fluid to be efficiently removed from the porous section of the liner.

The liner porous section may be made by forming a large number of perforations in the impermeable material of the liner, the perforations passing through the liner from its outer surface to its inner surface. Alternatively, the liner may be made of two materials, the porous section being made of a porous material which is joined to the impermeable material of the remainder of the liner. There may be more than one porous section.

In a particularly preferred embodiment of the invention, the liner is in the form of a hollow container dimensioned to fit over the residual limb portion, especially a below-knee residual limb portion of a transtibial amputee. The porous section or sections of the liner forms the distal portion of the liner. However, it is also possible, within the scope of the invention, to form the liner as a sleeve with proximal and distal open ends for the purpose of attaching an orthosis to a limb. In another embodiment of the invention, the liner is in the form of a cup or a dished patch for application to, for instance, the residuum of a through-hip amputee. In each case, the liner system is intended for use with an outer component in the form of the wall member to which a prosthesis or orthosis is attached, the wall member covering the porous section or sections of the liner and overlapping a peripheral edge or edges of the distribution layer to form a seal against the outer surface of the liner adjacent its peripheral edge or edges. In this way, when air is evacuated through a port in the wall member, the wall member is drawn onto the liner and, by virtue of the transmission of reduced pressure through the porous section, the liner is, itself, drawn onto the residuum, the space between the wall member and the liner being evacuated over the whole area of the distribution layer, the peripheral edge or edges of which are located to leave an exposed peripheral sealing portion or portions of the liner outer surface. The distribution layer extends over the whole of the liner porous section and beyond the boundary or boundaries of the porous section.

In the case of a liner system for enclosing a residual limb portion, the porous section or sections of the liner form a distal portion or portions thereof, extending from a distal end of the liner to an annular porous section boundary such that at least the distal third of the liner is porous (calculated as a fraction of the average length of the liner from its distal end to the rim. It is also possible for the extreme distal end to be impermeable and non-porous but for the major part of the liner distal portion to be porous.

As to the material of the liner it may, typically, be manufactured from a silicone material, from a urethane-based material, or from a gel such as tetrabutylstyrene gel.

The distribution layer is typically a synthetic fibre weave which may be integrated in the outer surface of the liner.

According to another aspect of the invention, a vacuum-assisted suspension device for a limb prosthesis or orthosis comprises: an air-impermeable outer component shaped to receive a human body portion; a flexible inner liner to be fitted over the body portion and having at least one peripheral edge, the liner being made of a material impermeable to air but having a porous section spaced from the or each peripheral edge to allow transmission of air and moisture between an outer surface and an inner surface of the liner; and a porous distribution layer sandwiched between the material of the liner and an inner surface of the outer component and adapted to allow transmission of air and moisture transversely over the said outer surface of the liner; the outer component having at least one air evacuation port to allow evacuation of air from the distribution layer. As stated above, the distribution layer typically extends over and beyond the porous section of the liner but is spaced from the or each peripheral edge of the liner to expose a border region of the liner outer surface. The component, typically in the form of a rigid outer wall member preferably covers the whole of the distribution layer and extends beyond the latter to engage the exposed outer surface between a peripheral edge of the distribution layer and the or each peripheral edge of the liner so as to form a substantially airtight seal against the liner.

In the case of the outer wall member being a hollow socket for receiving a residual limb portion, the inner liner comprises a hollow container with an open proximal end and a proximal closed distal end, the porous section of the liner comprising a distal portion thereof, with the distribution layer comprising a fabric sock between the outer surface of the liner and the inner surface of the socket. The port, in this case, is preferably in the form of a pipe union in a distal end portion of the socket, and may incorporate a non-return valve oriented to maintain a vacuum inside the socket once air has been evacuated.

According to a third aspect of the invention there is provided a vacuum-assisted suspension device for a limb prosthesis or orthosis comprising a hollow air-impermeable outer container shaped to receive a human limb portion; a flexible inner liner to be fitted over the body portion and having at least one peripheral edge, the liner being made of a material impermeable to air; and a porous distribution layer between the material of the liner and an inner surface of the wall member and adapted to allow transmission of air transversely over an outer surface of the liner; the container having at least one air evacuation port to allow evacuation of air from the distribution layer; wherein the distribution layer has at least one peripheral edge, the or each such edge being spaced from the peripheral edge or edges of the liner to leave at least one outer sealing portion on the liner outer surface, and wherein the container is shaped and sized so as to cover the distribution layer and to extend beyond the latter to engage and seal against the outer surface of the liner between the peripheral edge or edges of the distribution layer and the peripheral edge or edges of the liner when air is evacuated from between the container and the liner via the evacuation port thereby to suspend the container on the liner.

It is a primary advantage of liner systems described in this specification that sweat is drawn away from the surface of the body portion to which it is applied, helping to maintain a drier interface with the liner. This can reduce the relative movement between the body portion and the wall member which improves an amputee's proprioception, and helps to avoid the other above-mentioned disadvantages of a moist environment. Relative movement is also reduced by arranging for a vacuum to be established directly between the tissue surface of the body portion and the surface of the wall member or socket. This, in turn, reduces the chance of the wall member abrading the skin of the body portion.

Summarising, in a preferred embodiment of the invention, for use with a lower limb prosthesis, the liner comprises a sock of impermeable material having perforations formed therethrough to allow transmission of a vacuum and fluid through the liner between an outer surface and an inner surface of the liner. A proximal part of the liner is non-porous in order to provide an air-tight peripheral seal around the residual body portion at a proximal end of the liner when air is evacuated from the socket. In another embodiment, that part of the sock having perforations formed therethrough is replaced by a section of air-permeable and fluid permeable material. In either case the liner wall thickness, at least in a distal part thereof, is at least 2 mm. In another embodiment a part of the distal part of the liner that would otherwise be porous is left non-porous to prevent vacuum being applied directly to hypersensitive tissue or to prevent the extraction of fluid from sensitive or adherent parts of the surface of the residual body portion.

According to a fourth aspect of the invention, there is provided a suspension device a for a limb prosthesis or orthosis, comprising: a hollow air-impermeable outer wall member shaped to receive a human limb portion; and a flexible inner liner to be fitted over the body portion and having at least one peripheral edge, the liner being made of a material impermeable to air but having at least one porous section spaced from the or each peripheral edge to allow transmission of air and moisture between an outer surface and an inner surface of the liner; the wall member having at least one air evacuation port to allow evacuation of air from between an inner surface of the wall member and an outer surface of the liner; wherein the wall member is shaped and sized so as to cover the porous section of the liner and to extend beyond the latter to engage and seal against the outer surface of the liner between the porous section thereof and the peripheral edge or edges of the liner to form, in use, a sealed enclosure between the wall member and the body portion, the enclosure including the liner porous section, such that when air is evacuated from the sealed enclosure via the evacuation port, the wall member (is secured to the liner.

The invention will now be described by way of example with reference to the drawings, in which.

Embodiments of the invention described herein each comprise a liner system which includes a shaped liner for intimate fitting over a body portion such as the stump of an amputated limb from which a limb prosthesis is to be suspended or such as a complete natural limb to which an orthosis is to be attached. The liner is made at least partly of a flexible air-impermeable material. However, a section of the liner spaced from its edge or edges is porous to allow transmission of a vacuum through the liner between an outer surface and an inner surface of the liner. Additionally, an outer surface of at least the porous section of the liner is directly covered by a porous distribution layer for transmitting air and fluid transversely over the outer surface of the liner. When the liner has been fitted to the body portion referred to above, with the distribution layer on its outer surface, a substantially rigid cup, sleeve, or socket, depending on the shape of the body portion in question, is applied over the liner and distribution layer to form a vacuum-assisted suspension device as will be described below. In the case of the body portion being the residual limb of an amputee, the component applied to the liner system is a hollow socket. The residual body portion, when fitted with the liner system, is inserted inside the socket which then forms part of a prosthetic device replacing the amputated limb portion.

Whether it is in the form of a socket, sleeve, cup or disc, the component which is secured to the above body portion over the liner system is in the form of a substantially rigid wall member. This wall member has an inner receiving surface sized and shaped to abut the outer surface of part of the body portion with the liner placed over. A port is formed in the wall member to allow evacuation of air and fluid from the space between it and the liner. A non-return valve permits the evacuation of air and fluid via the port and can be used to maintain a vacuum between the wall member and the body portion. The valve may be incorporated in an evacuation pipe for connection to a vacuum pump.

An active vacuum region is created directly between the wall member and the tissue of the body portion adjacent the porous section of the liner, air being withdrawn via the port using the pump. The remainder of the liner is air-impermeable and forms a boundary of the evacuated region by creating a peripheral seal both between the liner and the body portion and between the liner and the wall member. The porous section of the liner allows transmission of air and fluid, for example, sweat, through the liner from the tissue of the body portion beneath the inner surface of the wall member. The porous distribution layer that covers the outer surface of the porous section of the liner allows transmission of the air and fluid between the outer surface of the liner and the inner surface of the wall member, and transversely and directly over the liner outer surface so that air is extracted from beneath the liner porous section to bring the skin of the body portion and the liner together, the extracted air being drawn to the port in the wall member via the distribution layer. At the same time, the liner and distribution layer are drawn against the inner surface of the wall member.

Figure 1:
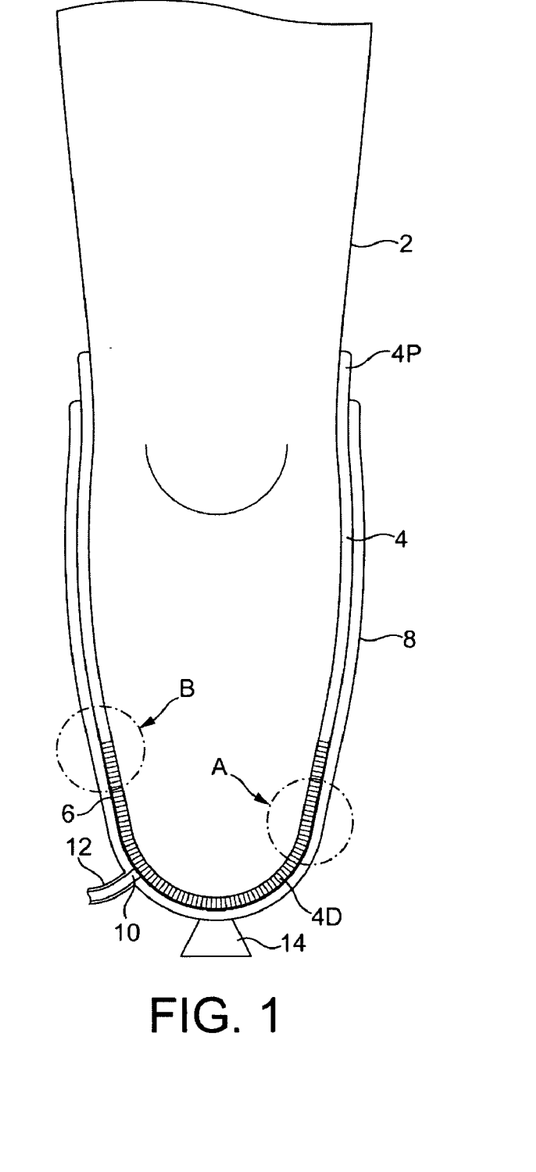
FIG. 1 is a partly-sectioned schematic view of a preferred vacuum suspension device in accordance with the invention, shown mounted to a lower limb residuum.
Figure 1A:
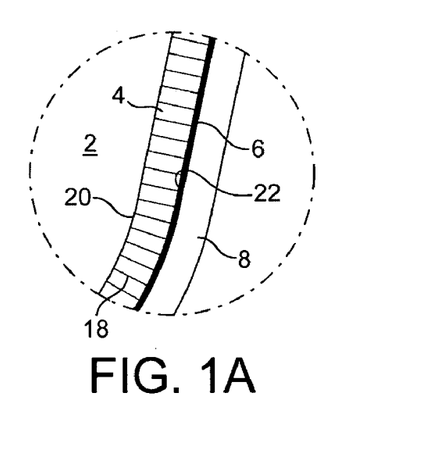
FIG. 1A is a detail as indicated by the arrow A in FIG. 1.

Referring to FIG. 1, a first liner system in accordance with the invention is for attaching a lower limb prosthesis to a lower limb residuum or stump 2. The liner system has a hollow liner 4 with a closed end and an open end which liner, in use, is fitted directly around the stump 2. As seen more particularly in FIG. 1A, applied directly to the outer surface of the liner 4 is a porous distribution layer 6 made of fabric or other air-permeable material allowing transmission of air transversely over the surface of the liner when the stump 2, fitted with the liner 4 and the distribution layer 6, is housed in a socket 8 of the lower limb prosthesis. The porous layer may be attached to the liner 4, integral with the liner or placed separately over the liner. The socket 8 is sized to receive all three of the stump 2, the liner 4 and the distribution layer 6 on the liner 4.

A port 10 is formed in a distal end portion of the wall of the socket 8, adjacent an interface 14 with the remainder of the prosthesis (not shown). The port 10 transmits air and fluid from the socket 8 via the port 10 through an evacuation pipe 12 connected via a pipe union to the socket wall. In this example, the interface 14 is a conventional pyramid-shaped spigot secured to the extreme distal end of the socket 8.

In this embodiment the material of the liner 4 is non-porous and air-impermeable. Silicone is the preferred material, but a flexible urethane or a tetrabutylstyrene gel (or similar) can be used. The liner comprises a proximal portion 4P with an open end and a distal portion 4D with a closed end. Formed in the distal portion 4D is a multiplicity of perforations 18, rendering the distal portion air- and fluid-permeable. The perforations 18 are distributed over the distal portion and each perforation 18 extends between an inner surface 20 and an outer surface 22 of the liner distal portion 4D substantially perpendicularly to these surfaces. The combination of perpendicularly oriented perforations 18 confining air and fluid transmission from the corresponding parts of the stump outwardly away from the stump surface and then transversely over the outside of the liner 4 through the distribution layer 6 efficiently draws the stump surface and the liner together when a vacuum pump is operated to withdraw air through the port 10 in the socket wall. Sweat is drawn directly away from the stump, helping to maintain a relatively dry stump/liner interface and maintaining intimate stump/liner contact. The vacuum created in the fabric distribution layer 6 between the liner 4 and the socket 8 draws the liner and the stump against the inner surface of the socket. In this way, the mechanical connection between the stump 2 and the socket 8 is improved, leading to improved proprioception. The lack of an intermediate layer between the liner and the stump minimises relative movement of the stump and the liner, results in easier cleaning of the liner, and avoids potential discomfort due to creasing of a fabric layer. As a further consequence, abrasion of the stump is reduced since relative movement of the stump within the socket is reduced and softening of the skin due to humidity is reduced.

The socket 8 is conventional insofar as it is made of a thermoplastics material such as a nylon based thermoplastics which is rigid compared to the liner, albeit with some resilience.

Figure 1B:
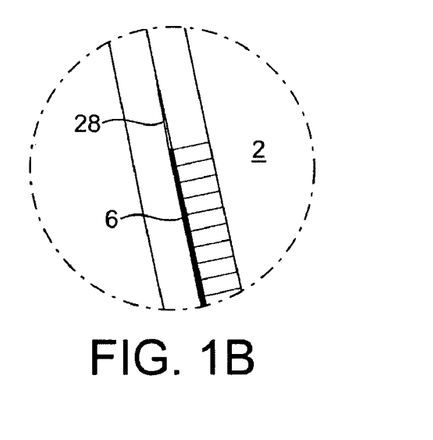
FIG. 1B is a detail as indicated by the arrow B in FIG. 1.

As shown more particularly in FIG. 1B, when air is evacuated from the socket 8, the boundary region 28 between the porous distal portion 4D and the impermeable proximal portion 4P of the liner 4 defines an airtight seal around the periphery of the stump by virtue of the impermeable nature of the proximal portion 4P which encircles the stump 2 and the fabric distribution layer 6 extending only over the distal portion 4D of the liner 4. As a result, the vacuum, preferably an active vacuum, created by pumping air from the port 10 holds the liner 4 to the socket 8 to provide suspension of the socket 8 from the stump 2 together with the remainder of the lower limb prosthesis (not shown) attached to the socket.

Figure 2:
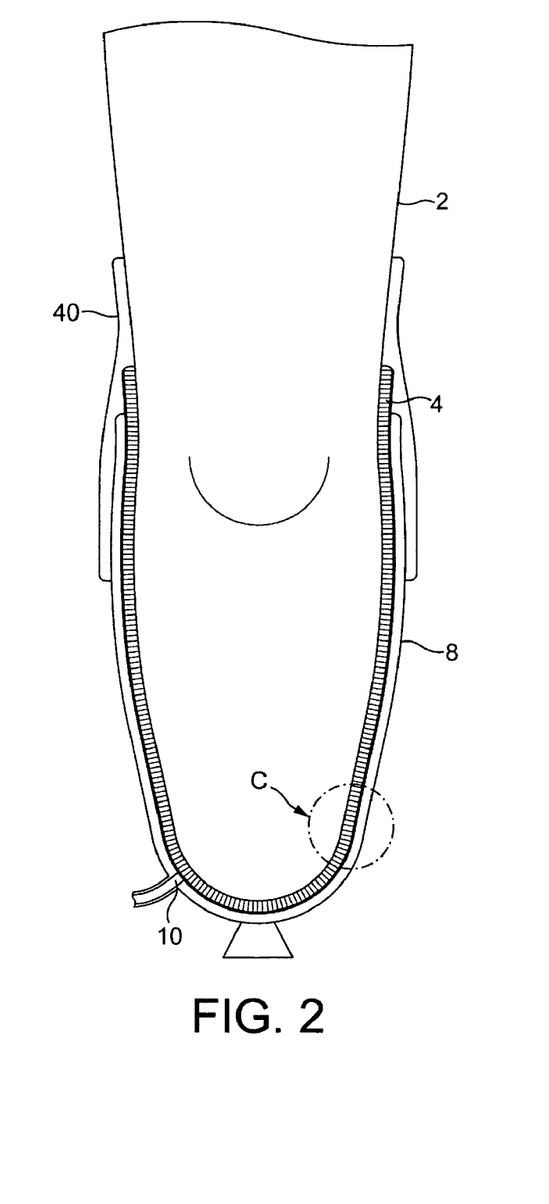
FIG. 2 is a partly-sectioned schematic view of an alternative vacuum suspension device in accordance with the invention, shown mounted to a lower limb residuum.
Figure 2A:
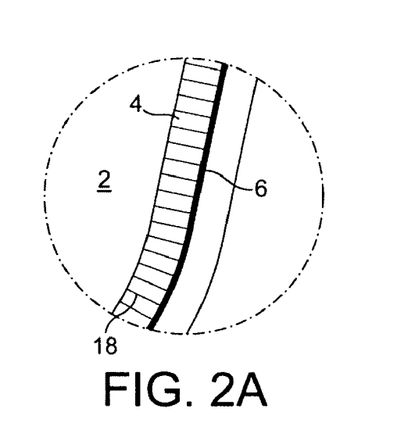
FIG. 2A is a detail as indicated by the arrow C in FIG. 2.

Referring to FIG. 2 and FIG. 2A, an alternative liner system in accordance with the invention has a liner 4 the whole of which, rather than just a distal portion, is formed with perforations 18 extending between the inner and outer surfaces. In this embodiment, the porous distribution layer 6 covers the complete outer surface of the liner 4. The effect of this structure is that air and fluid is drawn from the whole of the enclosed residual body portion or stump 2, through the liner 4. As before, the distribution layer 6 allows a substantially uniform pressure drop over the perforated area of the liner 4.

In this embodiment, to achieve suspension of the prosthesis from the stump 2, the interior of the socket is sealed by an annular sleeve 40 positioned proximally around the stump 2 and overlapping the proximal peripheries of both the socket 8 and the liner 4. The sleeve 40 is made of an air-impermeable material, such as silicone or urethane. It is important that the sleeve 40 fits closely over the stump 2, the liner 4 and the socket 8 so that when the socket 8 is evacuated, an airtight seal is formed between the stump and the socket.

As discussed above with reference to the prior art, an amputee may suffer negative consequences as a result of fluid forming on the surface of the stump 2. There is a variety of reasons why fluid may form, for example, sweat may be produced as a result of an increase in ambient temperature or because of physical exertion. Additionally, other body fluids may be produced on the surface of the stump, for example, by a wound.

Removal of fluid, by suction from the port 10, via the liner perforations and the distribution layer reduces relative movement between the stump and the socket and, avoids the formation of a moist environment which would soften the skin and provide an ideal breeding ground for pathogens. This is advantageous as a moist environment would make the residual body portion more prone to abrasion, tissue breakdown and infection. Furthermore, in the case of some wounds, the removal of fluid from the surface of the stump promotes healing.

Figure 3:
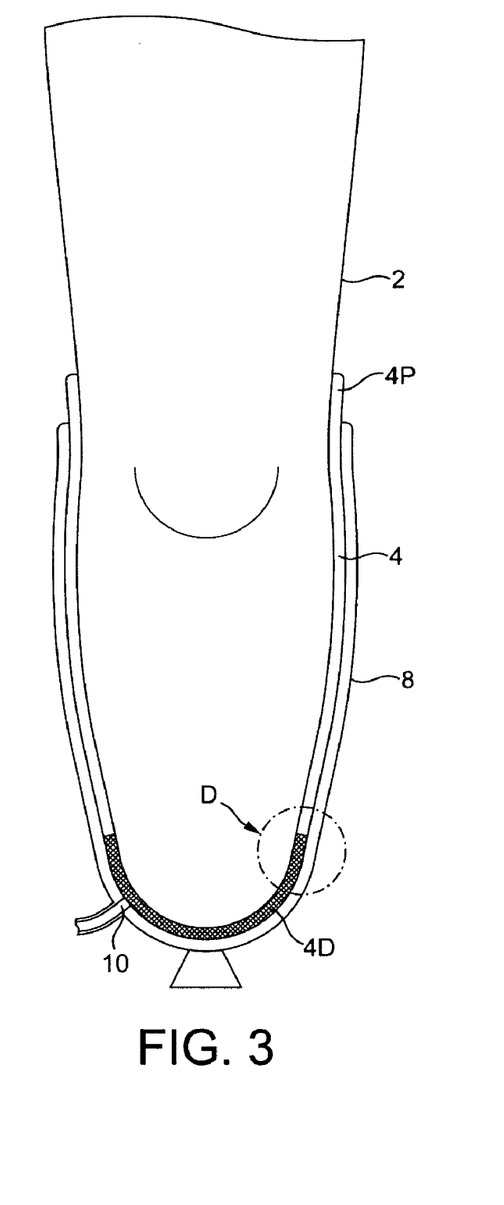
FIG. 3 is a partly-sectioned schematic view of a third vacuum suspension device in accordance with the invention, shown mounted to a lower limb residuum.
Figure 3A:
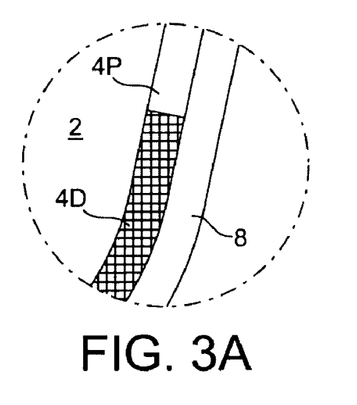
FIG. 3A is a detail as indicated by the arrow D in FIG. 3.

In a further alternative embodiment, as shown in FIG. 3 and FIG. 3A, the liner distal portion 4D is formed of an inherently porous material rather than an air impermeable material having multiple perforations. A fabric may be used as the porous material. An open cell foam or a felt having a smooth surface may also be used; however, it is best if the chosen material does not absorb fluids so as to avoid creating a breeding ground for pathogens. A Goretex® like fabric having a very closely woven surface is suitable. Additionally, as the distal portion 4D is porous, it can transmit air and fluid from the surface of the stump 2 to the port 10 and transversely within the liner distal portion 4D itself. Therefore, no porous outer distribution layer is needed.

Figure 4:
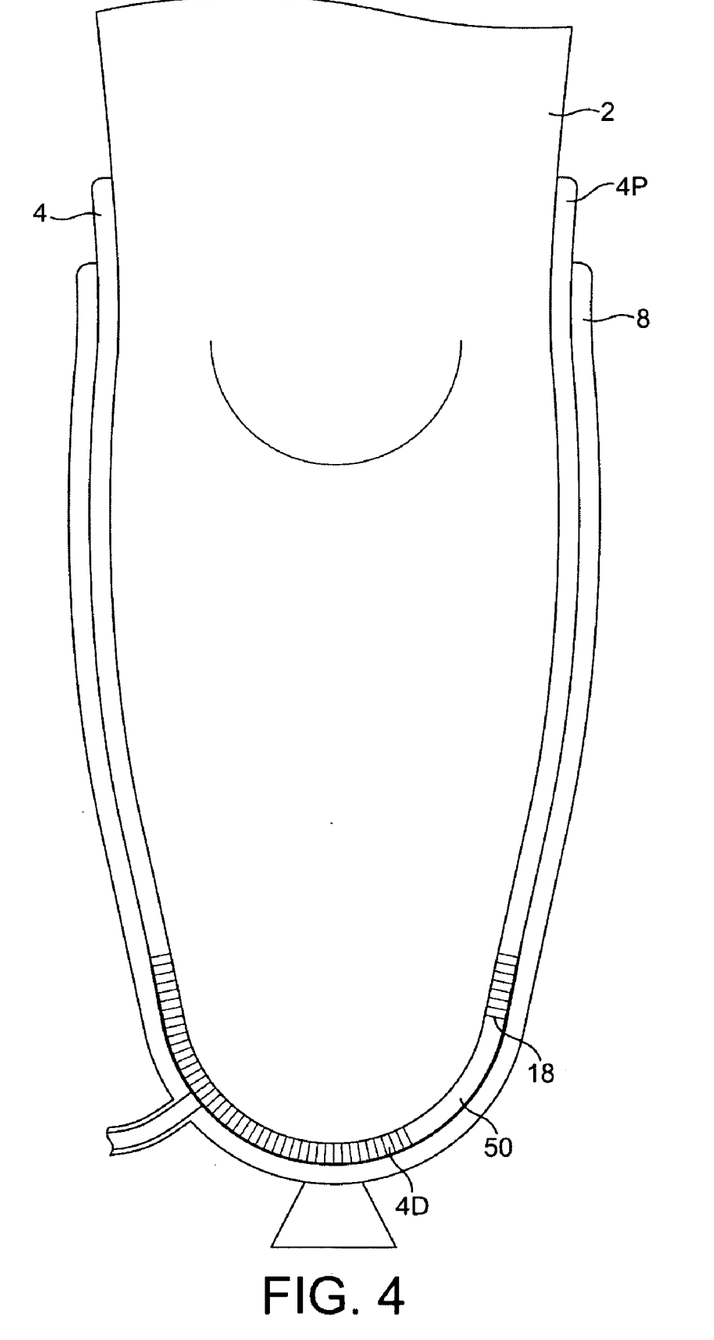
FIG. 4 is a partly-sectioned schematic view of a fourth vacuum suspension device in accordance with the invention, shown mounted to a lower limb residuum.

In a further variation, shown in FIG. 4, the distal portion 4D of the liner 4 is perforated but has a section 50 without perforations 18. Section 50 is, therefore, impermeable to air and fluid and can be used to protect a sensitive or adherent area of the stump. (This may be because the area is particularly bony or is otherwise unsuitable for being subject to an active vacuum, e.g. owing to hypersensitivity or a possibility of adherence.) The size, shape and location of the impermeable section 50 can be customised according to the sensitive or adherent area. However, the surface area of the remaining, porous part of the distal portion 4D is sufficient to create a vacuum over a large enough area to secure the liner 4 to the stump 2.

Figure 5:
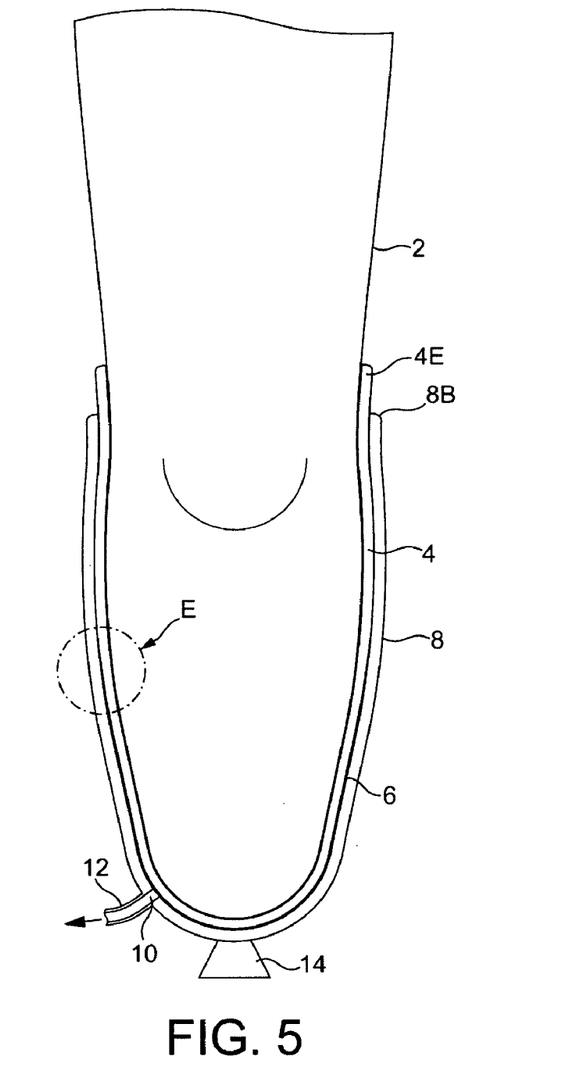
FIG. 5 is a partly-sectioned schematic view of a fifth vacuum suspension device in accordance with the invention, shown mounted to a lower limb residuum.
Figure 5A:
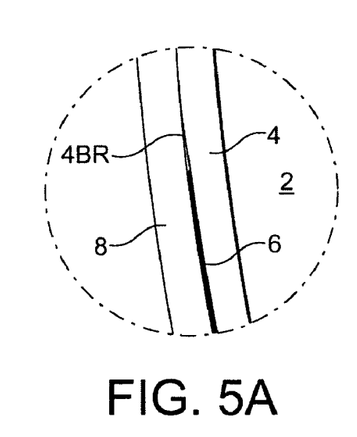
FIG. 5A is a detail as indicated by the arrow E in FIG. 5.

Referring to FIGS. 5 and 5A, the invention includes a novel suspension system which may be used when moisture removal from the stump 2 is considered to be inessential. In this embodiment, the liner 4 is made of a flexible impermeable material, but has no porous section, whether in the form of a section with perforations or a section of permeable material. As in previously described embodiments, the socket 8 is made of a substantially rigid thermoplastics or laminated material and is sized and shaped according to the size and shape of the stump 2. Sandwiched between the liner 4 and the socket 8 is a porous distribution layer 6 spaced from the peripheral edge of the brim 8B of the socket 8 so that the socket 8 and the liner 4 are in intimate sealing contact in a boundary region 4BR proximally of the distribution layer 6 and adjacent the brim 8B of the socket 8. The port 10 in the wall of the socket is in registry with the distribution layer (as in previously described embodiments) in order that air may be withdrawn efficiently from between the socket 8 and the liner 4 through the distribution layer 6. Such evacuation, and the intimate contact between the liner 4 and the stump 2 draws the socket 8 onto the combination of the liner and the stump so that the assembly acts as a suspension device for limb apparatus attached to the stump interface pyramid component 14. It will be noted that the peripheral edge 4E of the liner 4 is preferably exposed beyond the outer edge or brim 8B of the socket B.

The particular embodiments of the invention described above are applicable to suspension of a prosthesis for a below-knee (transtibial) amputee. However, it should be noted that the invention also encompasses a liner system and socket assembly for an above-knee prosthesis (transfemoral); and for an above- or below-elbow prosthesis. Moreover, embodiments of the invention may be used to secure a device at the site of a shoulder or hip, or other body site. Such an embodiment comprises a liner and a dish-shaped socket. Operation of this embodiment is equivalent to the embodiments described above with reference to FIGS. 1 to 5. The invention may be used in connection with the suspension of the limb prosthesis or orthosis from any body portion which is suitably sized and shaped for a sufficiently large vacuum area to be created to secure a suspension device.

Figure 6A:
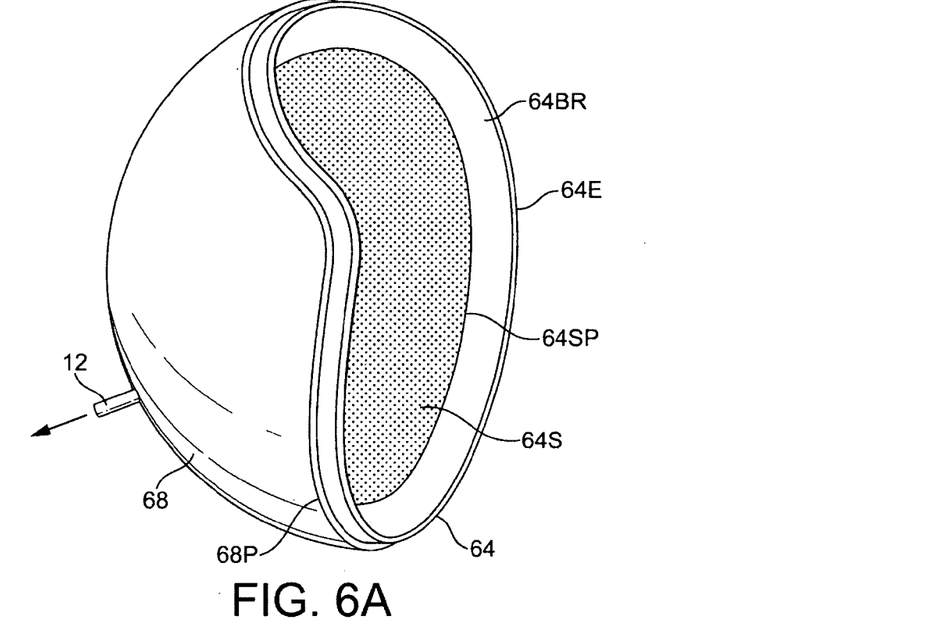
FIGS. 6A and 6B are, respectively, a perspective view of a sixth vacuum suspension device in accordance with the invention, intended for mounting to a hip disarticulation residuum, and a sectioned schematic view of the sixth suspension device, shown mounted to the hip disarticulation residuum.
Figure 6B:
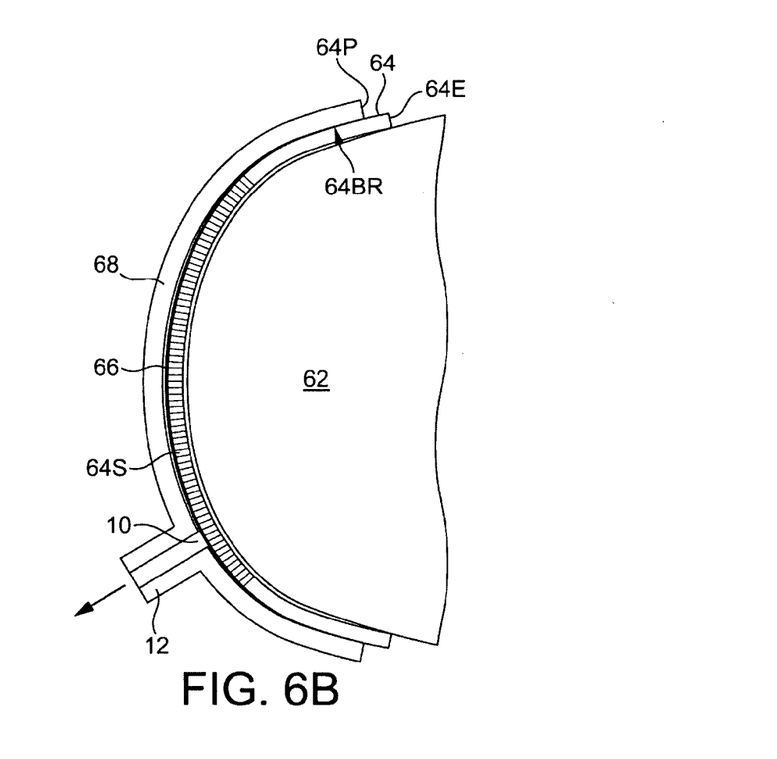

For instance, referring to FIGS. 6A and 6B, a substantially rigid dish-shaped wall member or receptacle 68 may be secured to a residual body portion 62 resulting from a hip or shoulder disarticulation. A flexible liner 64, also dish-shaped, is applied directly to the body portion 62. As in previously described embodiments, the liner is made of an air-impermeable material and has a porous section 64S the periphery 64SP of which is spaced from the peripheral edge 64E of the liner 64 to leave a non-porous boundary region 64BR surrounding the porous section 64S. The receptacle 68 is sized such that its own peripheral edge 68P and the annular edge portions adjacent the peripheral edge 68P is in registry with the boundary region of the liner when the receptacle 68 is applied to the liner 64. As in previously described embodiments, there is a fabric distribution layer overlying the porous section 64S of the liner, the periphery of the distribution layer 66 being spaced inwardly from the peripheral edge of the receptacle 68 to allow intimate sealing contact of the receptacle 68 with the boundary region 64BR of the liner 64, as shown in FIG. 6B.

As before, the receptacle 68 has an evacuation port 10 in registry with the distribution layer 66 and the porous section 64S of the liner 64.

Evacuation of air through the port 10 evacuates the space between the receptacle 68 and the liner 64, air being conducted transversely within the space by the distribution layer 66. At the same time, air is withdrawn from between the liner 64 and the body portion 62 through the perforated area of the liner and, in this way, the receptacle 68 is secured to the body portion 62 so that it can act as a mounting component for limb apparatus in the form of a prosthetic limb. The perforations in the liner 64 and the distribution layer 66 assist in drawing moisture away from the body portion 62.

A similar suspension device may be used for an orthosis.

It is also possible to construct the receptacle as a tubular sleeve to suspend an orthosis which encircles a limb with a tubular distribution layer and tubular layer beneath.

Embodiments of the invention have been described above with reference to an active vacuum created by a vacuum pump connected to the evacuation pipe. The vacuum pump may be a battery-powered pump or a purely mechanical pump powered by movement of a prosthesis or orthosis. However, it should be noted that in alternative embodiments within the scope of the invention a vacuum may be created without a vacuum pump by using a one-way valve connected to the evacuation pipe. The one-way valve is arranged to maintain a vacuum within the socket during a swing phase by allowing air and fluid to exit the socket but not enter the socket. Additionally, as air and fluid are not actively sucked out in this embodiment it may be necessary, depending on the specific application, to increase the size of the perforations in the liner to ensure that a vacuum is effectively transmitted.

The invention claimed is:

1. A vacuum-assisted liner system for use in a suspension device which is to be attached to a human body portion forming part of or associated with a limb, wherein the liner system comprises:

a flexible liner to be fitted over the body portion and having at least one peripheral edge, the liner being made of a material impermeable to air but having a section which is porous to allow transmission of air and moisture between an outer surface and an inner surface of the liner; and a porous distribution layer overlying the outer surface of the liner and adapted to allow transmission of air and moisture transversely over the said outer surface through the layer.

2. A liner system according to claim 1, wherein the porous section of the liner is formed by a section of the impermeable material having perforations formed therethrough.

3. A liner system according to claim 1, wherein the porous section of the liner is formed by a section of air-permeable material.

4. A liner system according to claim 1, wherein the liner is shaped to surround a human limb portion, wherein the distribution layer surrounds the liner and extends over the porous section of the liner.

5. A liner system according to claim 1, wherein the porous section is spaced from the or each peripheral edge.

6. A liner system according to claim 5, wherein the distribution layer has at least one peripheral edge, the or each peripheral edge of the distribution layer being spaced from the peripheral edge or edges of the liner to leave at least one exposed peripheral sealing portion on the liner outer surface.

7. A liner system according to claim 5, for enclosing a residual limb portion, and having a distal closed end and a proximal open end, the open end being defined by a single said peripheral edge of the liner, wherein the porous section of the liner forms a distal portion thereof.

8. A vacuum-assisted suspension device for a limb prosthesis or orthosis, comprising:

an air-impermeable outer wall member shaped to receive a human body portion;

a flexible inner liner to be fitted over the body portion and having at least one peripheral edge, the liner being made of a material impermeable to air but having a section which is porous to allow transmission of air and moisture between an outer surface and an inner surface of the liner; and a porous distribution layer sandwiched between the material of the liner and an inner surface of the wall member and adapted to allow transmission of air and moisture transversely over the said outer surface of the liner;

the wall member having at least one air evacuation port to allow evacuation of air from the distribution layer.

9. A vacuum-assisted suspension device according to claim 8, wherein the porous section is spaced from the or each peripheral edge.

10. A suspension device according to claim 9, wherein the distribution layer extends over and beyond the porous section of the liner but is spaced from the or each peripheral edge of the liner, and wherein the wall member covers the distribution layer and extends beyond the latter to engage the outer surface of the liner between the distribution layer and the or each peripheral edge of the liner so as to form a substantially airtight seal against the liner.

11. A suspension device according to claim 9, wherein the outer wall member is a hollow socket for receiving a residual limb portion, the inner liner comprises a hollow container with an open proximal end and a closed distal end, the porous section or sections of the liner comprising a distal portion thereof, and the distribution layer comprises a fabric sock between the outer surface of the liner and the inner surface of the socket.

12. A suspension device for a limb prosthesis or orthosis, comprising:
- a hollow air-impermeable outer wall member shaped to receive a human limb portion; and
- a flexible inner liner to be fitted over the limb portion and having at least one peripheral edge, the liner being made of a material impermeable to air but having at least one porous section spaced from the or each peripheral edge to allow transmission of air and moisture between an outer surface and an inner surface of the liner;
- the wall member having at least one air evacuation port to allow evacuation of air from between an inner surface of the wall member and an outer surface of the liner;
- wherein the wall member is shaped and sized so as to cover the porous section of the liner and to extend beyond the latter to engage and seal against the outer surface of the liner between the porous section thereof and the peripheral edge or edges of the liner to form, in use, a sealed enclosure between the wall member and the body limb portion, the enclosure including the liner porous section, such that when air is evacuated from the sealed enclosure via the evacuation port, the wall member is secured to the liner.

* * * * *